United States Patent
Braido et al.

(10) Patent No.: US 10,070,954 B2
(45) Date of Patent: Sep. 11, 2018

(54) MITRAL HEART VALVE REPLACEMENT

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US); Thomas M. Benson, Minneapolis, MN (US); Theodore Paul Dale, Corcoran, MN (US); Andrea N. Para, St. Louis, MO (US); Mark Krans, Hopkins, MN (US); Mathias Charles Glimsdale, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 110 days.

(21) Appl. No.: 15/076,854

(22) Filed: Mar. 22, 2016

(65) Prior Publication Data

US 2016/0278922 A1    Sep. 29, 2016

Related U.S. Application Data

(60) Provisional application No. 62/137,411, filed on Mar. 24, 2015.

(51) Int. Cl.
*A61F 2/24* (2006.01)
*A61F 2/89* (2013.01)

(52) U.S. Cl.
CPC .............. *A61F 2/2469* (2013.01); *A61F 2/24* (2013.01); *A61F 2/2409* (2013.01);
(Continued)

(58) Field of Classification Search
CPC ........ A61F 2/24; A61F 2/2418; A61F 2/2409; A61F 2220/0008
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

"Closed heart surgery: Back to the future", Samuel V. Lichtenstein, The Journal of Thoracic and Cardiovascular Surgery, vol. 131, No. 5, pp. 941-943.

(Continued)

*Primary Examiner* — Dinah Baria
(74) *Attorney, Agent, or Firm* — Lerner, David, Littenberg, Krumholz & Mentlik, LLP

(57) ABSTRACT

A prosthetic heart valve having an inflow end and an outflow end includes a collapsible and expandable stent including a plurality of cells arranged in rows extending around a circumference of the stent, at least one of the rows forming a flared portion having a diameter that is larger than diameters of others of the rows. The stent further includes engaging arms disposed adjacent the outflow end and extending toward the inflow end, the engaging arms being configured to couple to heart tissue to anchor the stent. A collapsible and expandable valve assembly has a plurality of leaflets disposed within the stent.

20 Claims, 15 Drawing Sheets

(52) U.S. Cl.
CPC .............. *A61F 2/2418* (2013.01); *A61F 2/89* (2013.01); *A61F 2220/0008* (2013.01); *A61F 2230/0069* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 8,840,663 B2 | 9/2014 | Salahieh et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2009/0192591 A1* | 7/2009 | Ryan .................. A61F 2/2412 623/1.26 |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |

(56) References Cited

U.S. PATENT DOCUMENTS

| | | | |
|---|---|---|---|
| 2011/0313515 A1* | 12/2011 | Quadri | A61F 2/2415 623/2.2 |
| 2012/0303116 A1 | 11/2012 | Gorman, III et al. | |
| 2014/0330371 A1 | 11/2014 | Gloss et al. | |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01/028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008549 A1 | 1/2010 |
| WO | 2010008548 A2 | 1/2010 |
| WO | 10096176 A1 | 8/2010 |
| WO | 10098857 A1 | 9/2010 |
| WO | 2012177942 A2 | 12/2012 |
| WO | 2014181336 A1 | 11/2014 |
| WO | 2015148241 A1 | 10/2015 |

OTHER PUBLICATIONS

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Apr. 24, 2006).

"Percutaneous Aortic Valve Implantation Retrograde From the Femoral Artery", John G. Webb et al., Circulation, 2006; 113:842-850 (Feb. 6, 2006).

"Transapical aortic valve implantation: an animal feasibility study"; Todd M. Dewey et al., The annals of thoracic surgery 2006; 82: 110-6 (Feb. 13, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical Transcatheter Aortic Valve Implantation in Humans", Samuel V. Lichtenstein et al., Circulation. 2006; 114: 591-596 (Jul. 31, 2006).

Catheter-implanted prosthetic heart valves, Knudsen, L.L., et al., The International Journal of Artificial Organs, vol. 16, No. 5 1993, pp. 253-262.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Percutaneous aortic valve replacement: resection before implantation, 836-840, Quaden, Rene et al., European J. of Cardio-thoracic Surgery, 27 (2005).

Ruiz, Carlos, Overview of PRE-CE Mark Transcatheter Aortic Valve Technologies, Euro PCR.

Textbook "Transcatheter Valve Repair", 2006, pp. 165-186.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

International Search Report for PCT/US2016/023518 dated Sep. 19, 2016.

* cited by examiner

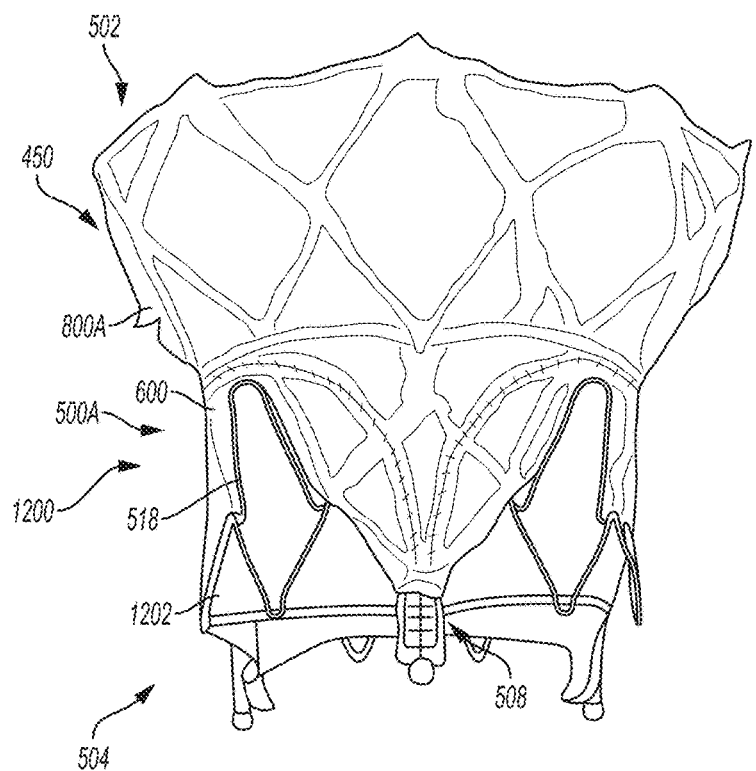
FIG. 12A
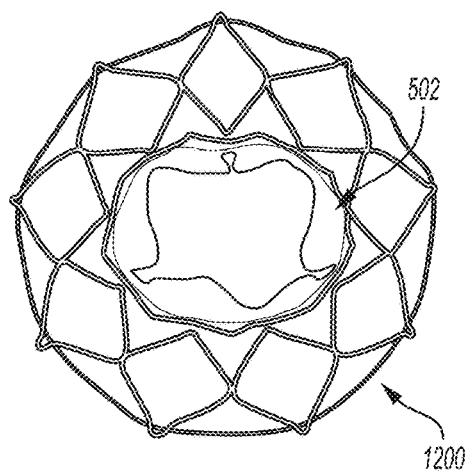
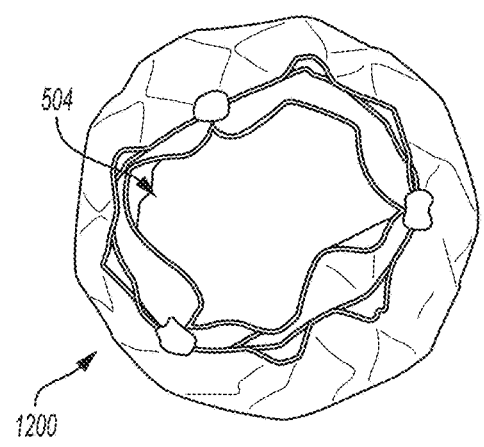
FIG. 12B   FIG. 12C

US 10,070,954 B2

MITRAL HEART VALVE REPLACEMENT

CROSS-REFERENCE TO RELATED APPLICATIONS

The present application claims the benefit of the filing date of U.S. Provisional Patent Application No. 62/137,411 filed Mar. 24, 2015, the disclosure of which is hereby incorporated herein by reference.

BACKGROUND OF THE INVENTION

The present disclosure relates to heart valve replacement and, in particular, to collapsible prosthetic heart valves. More particularly, the present disclosure relates to devices and methods for replacing the functionality of a native mitral valve.

Diseased and/or defective heart valves may lead to serious health complications. One method of addressing this condition is to replace a non-functioning heart valve with a prosthetic valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve having an inflow end and an outflow end includes a collapsible and expandable stent including a plurality of cells arranged in rows, each of the rows extending around a circumference of the stent, at least one of the rows forming a flared portion having a diameter that is larger than diameters of others of the rows, the stent further including engaging arms disposed adjacent the outflow end and extending toward the inflow end, the engaging arms being configured to couple to heart tissue to anchor the stent. A collapsible and expandable valve assembly is disposed within the stent and having a plurality of leaflets.

In some embodiments a prosthetic heart valve having an inflow end and an outflow end, includes a collapsible and expandable stent including a plurality of cells arranged in rows, each of the rows extending around a circumference of the stent, the rows including a first row of having a first diameter and a second row of cells having a second diameter, the second diameter being larger than the first diameter, a collapsible and expandable valve assembly disposed within the stent and having a plurality of leaflets, an annular cuff disposed over cells of the first row of cells, and an annular skirt disposed over cells of the second row of cells.

BRIEF DESCRIPTION OF THE DRAWINGS

Various embodiments of the present disclosure are disclosed herein with reference to the drawings, wherein:

FIGS. 12A-C are photographs showing the side, top and bottom, respectively, of a fully assembled prosthetic heart valve;

Various embodiments of the present disclosure will now be described with reference to the appended drawings. It is to be appreciated that these drawings depict only some embodiments of the disclosure and are therefore not to be considered limiting of its scope.

DETAILED DESCRIPTION

In conventional collapsible prosthetic heart valves, the stent is usually anchored within the native valve annulus via radial forces exerted by the expanding stent against the native valve annulus. If the radial force is too high, damage may occur to heart tissue. If, instead, the radial force is too low, the heart valve may move from its implanted position, for example, into the left ventricle. Because such anchoring partly depends on the presence of calcification or plaque in the native valve annulus, it may be difficult to properly anchor the valve in locations where plaque is lacking (e.g., the mitral valve annulus). Additionally, in certain situations it may be preferable to restore native valve leaflet function instead of implanting a prosthetic device to replace that function.

In view of the foregoing, there is a need for further improvements to the devices, systems, and methods for replacing the function of a native heart valve, such as a mitral valve, a tricuspid valve, an aortic valve, or a pulmonary valve. Among other advantages, the present disclosure may address one or more of these needs. While many of the examples are described herein with reference to a specific valve (e.g., a mitral valve or a tricuspid valve), it will be understood that many of the examples are not so limited and that the concepts described apply equally to other heart valves unless expressly limited herein.

Blood flows through the mitral valve from the left atrium to the left ventricle. As used herein, the term "inflow," when used in connection with a prosthetic mitral heart valve, refers to the end of the heart valve closest to the left atrium when the heart valve is implanted in a patient, whereas the term "outflow," when used in connection with a prosthetic mitral heart valve, refers to the end of the heart valve closest to the left ventricle when the heart valve is implanted in a patient. When used in connection with a prosthetic aortic valve, "inflow" refers to the end closest to the left ventricle and "outflow" refers to the end closest to the aorta. The same convention is applicable for other valves wherein "inflow" and "outflow" are defined by the direction of blood flow therethrough. Also, as used herein, the words "substantially," "approximately," "generally" and "about" are intended to mean that slight variations from absolute are included within the scope of the structure or process recited.

Figure 1:
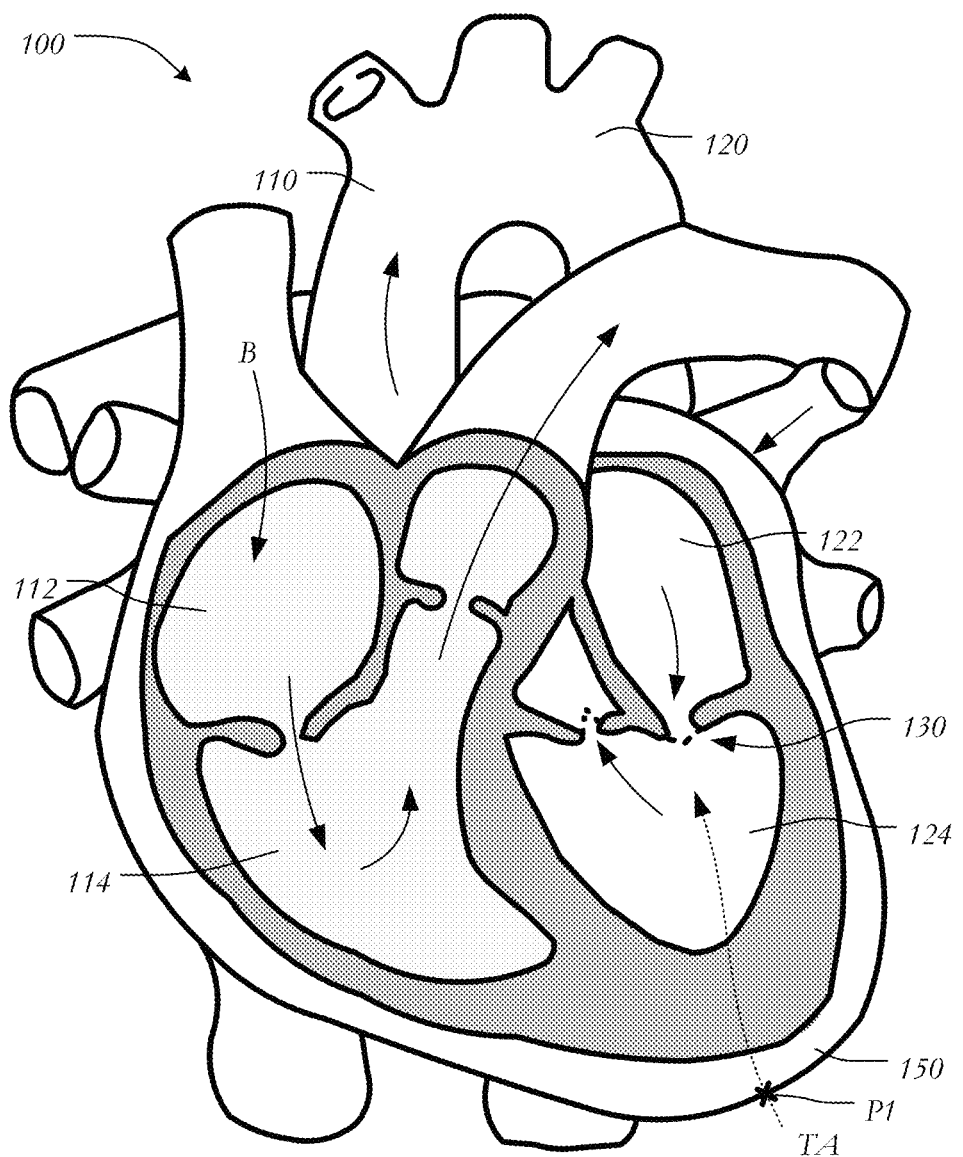
FIG. 1 is a schematic representation of a human heart showing a transapical delivery approach.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium and the left ventricle is the mitral valve 130. The mitral valve 130, also known as the bicuspid valve or left atrioventricular valve, is a dual-flap that opens as a result of increased pressure in the left atrium as it fills with blood. As atrial pressure increases above that of the left ventricle, the mitral valve opens and blood passes toward the left ventricle. Blood flows through heart 100 in the direction shown by arrows "B".

A dashed arrow, labeled "TA", indicates a transapical approach for repairing or replacing heart valves, such as a mitral valve. In transapical delivery, a small incision is made between the ribs and into the apex of the left ventricle 124 at position "P1" in heart wall 150 to deliver a prosthesis or device to the target site.

Figure 2A:
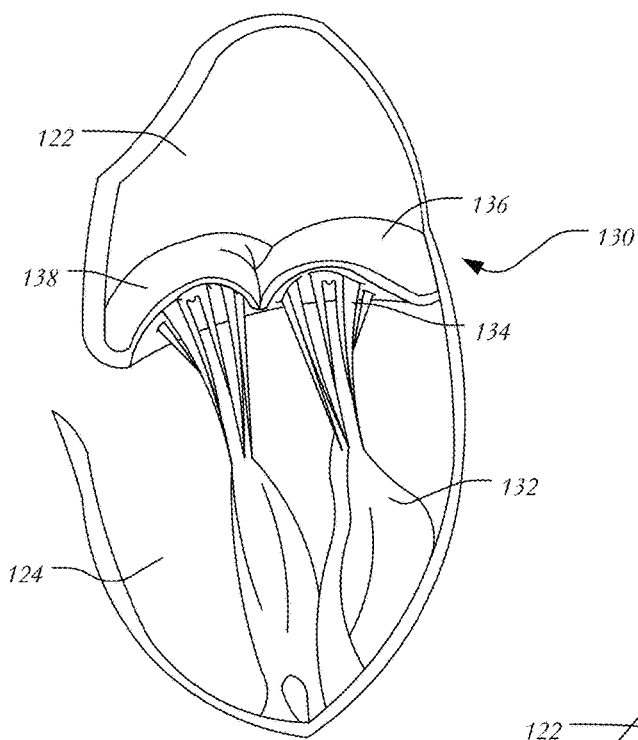
FIG. 2A is a schematic representation of a native mitral valve and associated structures during normal operation.

FIG. 2A is a more detailed schematic representation of a native mitral valve 130 and its associated structures. Mitral valve 130 includes two flaps or leaflets, a posterior leaflet 136 and an anterior leaflet 138, disposed between left atrium 122 and left ventricle 124. Cord-like tendons known as chordae tendineae 134 connect the two leaflets 136, 138 to the medial and lateral papillary muscles 132. During atrial systole, blood flows from the left atrium to the left ventricle down the pressure gradient. When the left ventricle contracts in ventricular systole, the increased blood pressure in the chamber pushes the mitral valve to close, preventing backflow of blood into the left atrium. Since the blood pressure in the left atrium is much lower than that in the left ventricle, the flaps attempt to evert to the low pressure regions. The chordae tendineae prevent the eversion by becoming tense, thus pulling the flaps and holding them in the closed position.

Figure 2B:
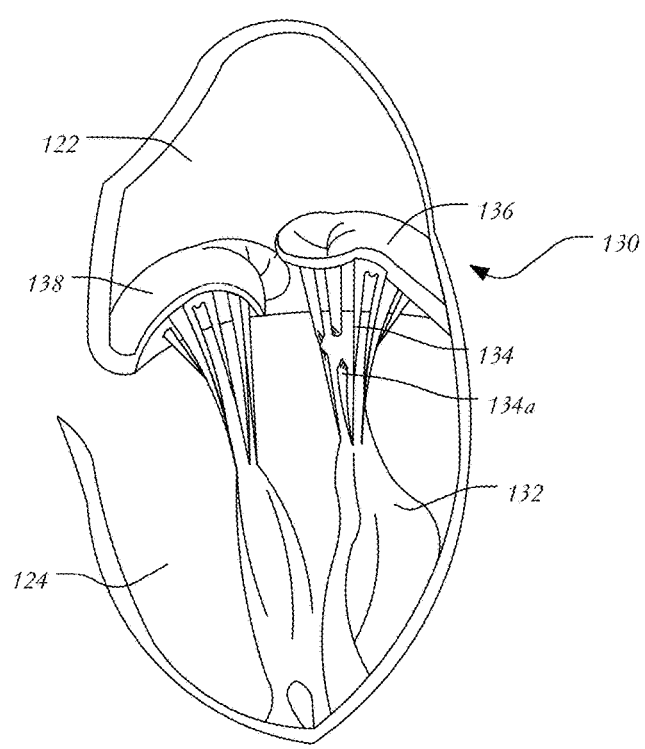
FIG. 2B is a schematic representation of a native mitral valve having a prolapsed leaflet.

FIG. 2B is a schematic representation of mitral valve prolapse as discussed above. Posterior leaflet 136 has prolapsed into left atrium 122. Moreover, certain chordae tendineae have stretched and others have ruptured. Because of damaged chordae 134a, even if posterior leaflet 136 returns to its intended position, it will eventually resume the prolapsed position due to being inadequately secured. Thus, mitral valve 130 is incapable of functioning properly and blood is allowed to return to the left atrium and the lungs. It will be understood that, in addition to chordae damage, other abnormalities or failures may be responsible for mitral valve insufficiency.

Figure 3:
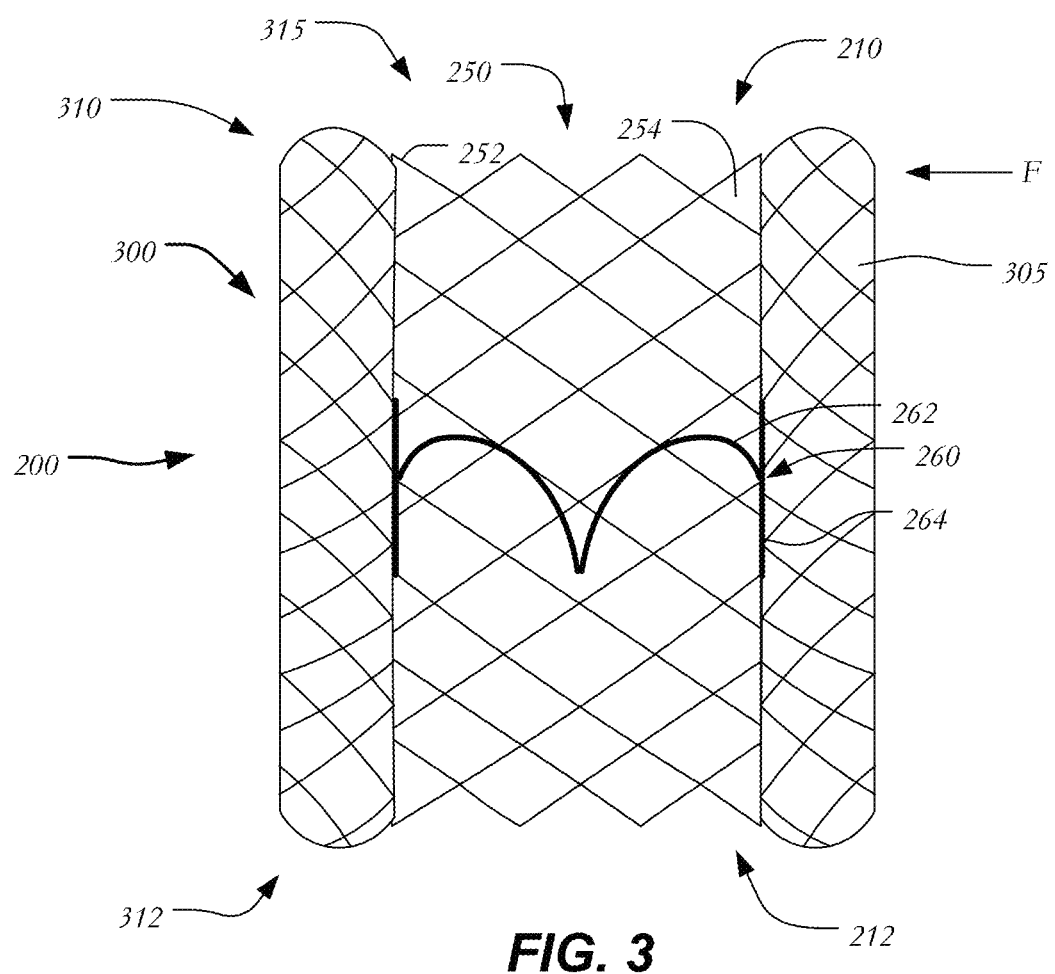
FIG. 3 is a schematic longitudinal cross-section of one embodiment of a prosthetic heart valve having a stent, a valve assembly, and a frame.

FIG. 3 is a longitudinal cross-section of prosthetic heart valve 200 in accordance with one embodiment of the present disclosure. Prosthetic heart valve 200 is a collapsible prosthetic heart valve designed to replace the function of the native mitral valve of a patient (see native mitral valve 130 of FIGS. 1-2). Generally, prosthetic valve 200 has inflow end 210 and outflow end 212. Prosthetic valve 200 may be substantially cylindrically shaped and may include features for anchoring, as will be discussed in more detail below. When used to replace native mitral valve 130, prosthetic valve 200 may have a low profile so as not to interfere with atrial function.

Prosthetic heart valve 200 includes stent 250, which may be formed from biocompatible materials that are capable of self-expansion, such as, for example, shape memory alloys including nitinol. Alternatively, stent 250 may be formed of a material suitable for balloon-expansion. Stent 250 may include a plurality of struts 252 that form cells 254 connected to one another in one or more annular rows around the stent. Cells 254 may all be of substantially the same size around the perimeter and along the length of stent 250. Alternatively, cells 254 near inflow end 210 may be larger than the cells near outflow end 212. Stent 250 may be expandable to provide a radial force to assist with positioning and stabilizing prosthetic heart valve 200 within the native mitral valve annulus.

Prosthetic heart valve 200 may also include valve assembly 260, including a pair of leaflets 262 attached to a cylindrical cuff 264. Leaflets 262 replace the function of native mitral valve leaflets 136 and 138 described above with reference to FIG. 2. That is, leaflets 262 coapt with one another to function as a one-way valve. It will be appreciated, however, that prosthetic heart valve 200 may have more than two leaflets when used to replace a mitral valve or other cardiac valves within a patient. Valve assembly 260 of prosthetic heart valve 200 may be substantially cylindrical, or may taper outwardly from outflow end 212 to inflow end 210. Both cuff 264 and leaflets 262 may be wholly or partly formed of any suitable biological material, such as bovine or porcine pericardium, or polymers, such as PTFE, urethanes and the like.

When used to replace a native mitral valve, valve assembly 260 may be sized in the range of about 20 mm to about 40 mm in diameter. Valve assembly 260 may be secured to stent 250 by suturing to struts 252 or by using tissue glue, ultrasonic welding or other suitable methods.

An optional frame 300 may surround and house valve assembly 260 and stent 250. Frame 300 may be formed of a braided material in various configurations to create shapes and/or geometries for engaging tissue and filling the spaces between valve assembly 260 and the native valve annulus. As shown in FIG. 3, frame 300 includes a plurality of braided strands or wires 305 arranged in three-dimensional shapes. In one example, wires 305 form a braided metal fabric that is both resilient and capable of heat treatment substantially to a desired preset shape. One class of materials which meets these qualifications is shape memory alloys. One example of a suitable shape memory alloy is Nitinol. It is also contemplated that wires 305 may comprise various materials other than Nitinol that have elastic and/or memory properties, such as spring stainless steel, alloys such as Elgiloy®, Hastelloy®, and MP35N®, CoCrNi alloys (e.g., trade name Phynox), CoCrMo alloys, or a mixture of metal and polymer fibers. Depending on the individual material selected, the strand diameter, number of strands, and pitch may be altered to achieve desired properties for frame 300.

In the simplest configuration of frame 300, shown in FIG. 3, frame 300 may be formed in a cylindrical or tubular configuration having inlet end 310, outlet end 312 and lumen 315 extending between inlet end 310 and outlet end 312 for housing stent 250 and valve assembly 260. However, in certain embodiments stent 250 may be omitted, and valve assembly 260 may be directly attached to frame 300 using any of the techniques described above for attaching valve assembly 260 to stent 250. Frame 300 may be radially collapsed from a relaxed or preset configuration to a compressed or reduced configuration for delivery into the patient. Once released after delivery, the shape-memory properties of frame 300 may cause it to re-expand to its relaxed or preset configuration. Frame 300 may also be locally compliant in a radial direction such that a force exerted in the direction of arrow F deforms a portion of the frame. In this manner, irregularities in the native valve annulus may be filled by frame 300, thereby preventing paravalvular leakage. Moreover, portions of frame 300 may endothelialize and in-grow into the heart wall over time, providing permanent stability and a low thrombus surface.

Figure 4:
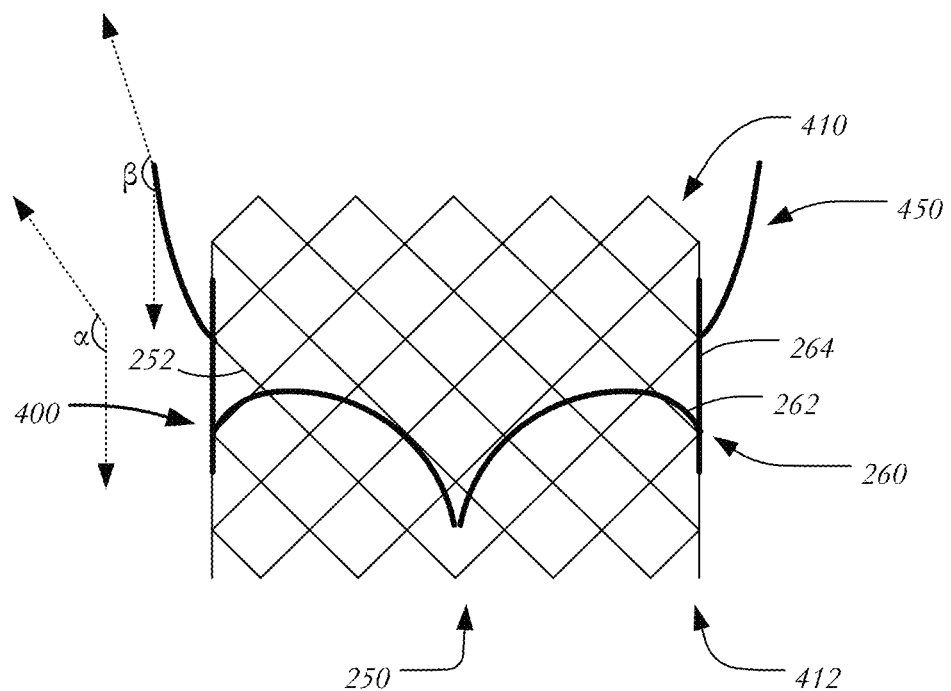
FIG. 4 is a schematic longitudinal cross-section of one embodiment of a prosthetic heart valve having a stent, a valve assembly, and a flared portion.

FIG. 4 illustrates one variation in which prosthetic heart valve 400 includes additional features to aid in fixing the valve at a predetermined location within the native valve annulus. Prosthetic heart valve 400 generally extends between inflow end 410 and outflow end 412 and includes all of the elements disclosed above including stent 250 formed of struts 252, valve assembly 260 having leaflets 262 and cuff 264. Stent 250 may be substantially cylindrical and may further include flared portion 450 adjacent inflow end 410 that projects radially outward from the cylindrical stent to anchor the stent at a predetermined location in the native valve annulus. Flared portion 450 forms an angle α with the longitudinal axis of stent 250. In some examples, angle α may be between about 80 degrees and about 180 degrees. In some examples, angle α may be between about 90 and 110 degrees. Moreover, as shown in FIG. 4, flared portion 450 may be curved. Thus, flared portion 450 may have an initial takeoff angle α and then round out along its length to form a second angle β with the longitudinal axis of stent 250 near its distal end. As a result of the rounding, second angle β may between about 160 degrees and about 180 degrees. During delivery, flared portion 450 may be compressed against the outside of collapsed stent 250 within a sheath of a delivery device and may return to its flared configuration when released from the sheath. When prosthetic heart valve 400 is used to replace the function of a native mitral valve, flared portion 450 may be disposed at least partially within the left atrium. Details of flared portion 450 are explored further below with reference to FIGS. 5A and 5B.

Figure 5A:
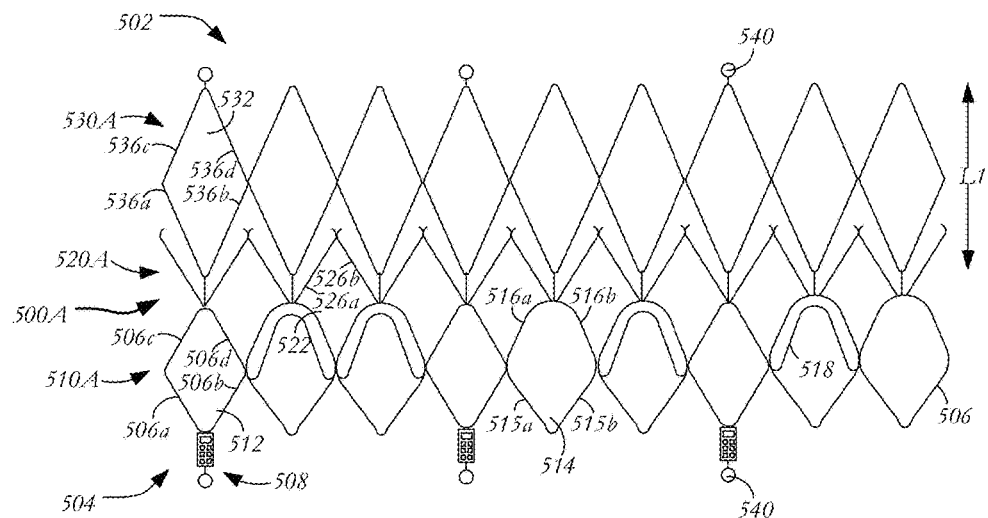
FIG. 5A is a developed view of one example of a stent having a flared portion and a plurality of engaging arms.

FIG. 5A is a developed view of a stent 500A suitable for use in a mitral heart valve prosthesis. Stent 500A generally extends in a length direction between inflow end 502 and outflow end 504 and includes a plurality of struts 506 forming rows of cells 510A, 520A, 530A, and a plurality of commissure features 508. First row of cells 510A is disposed adjacent outflow end 504 and includes symmetric cells 512, typically disposed adjacent commissure features 508, and asymmetric cells 514 at selected positions within first row 510A. Symmetric cells 512 may be substantially diamond-shaped and include four substantially straight struts 506a-d of substantially equal length. Asymmetric cells 514 may include a pair of substantially straight struts 515a, 515b which form a V-shape attached to substantially curved struts 516a, 516b. Nested within selected ones of asymmetric cells 514 are engaging arms 518, which extend generally from the connection of one cell 514 to the adjacent cells in either side thereof in row 510A, and which have a curved shape which generally follows the curved shape of struts 516a, 516b. Engaging arms 518 may be configured to engage portions of heart tissue by contacting, clasping, gripping, securing or otherwise preventing, minimizing or limiting the motion of stent 500A (e.g., native mitral valve leaflets) when the stent is deployed in a patient as part of a prosthetic heart valve. Second row of cells 520A may include a plurality of cells 522 formed by two struts shared with cells from first row 510A (e.g., struts 506c, 506d, 516a, 516b) and two substantially straight struts 526a, 526b. A third row of cells 530A includes enlarged cells 532 formed of struts 536a-d, each of which is longer than struts 506a-d. Third row 530A may include cells that have a length L1 that is greater than the lengths of other cells. In at least some examples, length L1 may be between about 20 mm and about 30 mm. Third row 530A of enlarged cells 532 may be configured to form a diameter greater than the diameter formed by the first two rows. Thus, as shown in the cross-sectional schematic of FIG. 4, when stent 500A fully expands, third row 530A of enlarged cells 532 forms a flared portion. Optionally, a number of retainers 540 may be disposed on selected enlarged cells 532 as well as on commissure features 508 to help hold stent 500A in the delivery apparatus and aid in its deployment.

As shown in FIG. 5A, stent 500A is formed of three rows of cells, each row having nine cells and is thus referred to as a nine-cell configuration. As briefly discussed, engaging arms 518 are nested within selected asymmetric cells 514 to engage the native valve leaflets. Because the native mitral valve includes two native leaflets, the illustrated example includes two engaging arms 518 for mating with each native valve leaflet, the first pair of engaging arms being spaced apart from the second pair of engaging arms so that they are approximately contralateral to one another. It will be understood, however, that in a nine-cell stent configuration, it may be difficult to provide pairs of engaging arms that are exactly 180 degrees apart from one another.

Figure 5B:
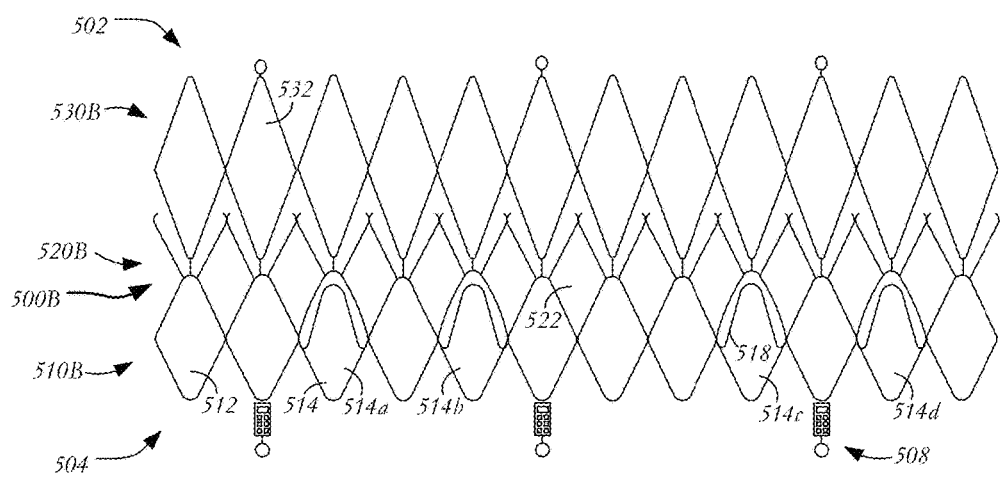
FIG. 5B is a developed view of another example of a stent having a flared portion and a plurality of engaging arms.

FIG. 5B shows a variation in which stent 500B has a twelve-cell configuration (i.e., each row of cells in stent 500B includes twelve cells). Stent 500B extends between inflow end 502 and outflow end 504 and includes a first row of cells 510B having symmetric cells 512 and asymmetric cells 514, a second row of cells 520B having cells 522 and a third row of cells 530B having enlarged cells 532. Engaging arms 518 are nested within two pairs of asymmetric cells 514a, 514b and 514c, 514d each pair of asymmetric cells being spaced from one another by a symmetric cell. In this example, pairs of engaging arms 518 are offset from one another as much as possible, and provide a generally more symmetric configuration than stent 500A, which allow for simpler coupling of the belly and leaflets. Thus, the positioning of the engaging arms may be affected by the number of cells in rows of a stent.

Figure 6A:
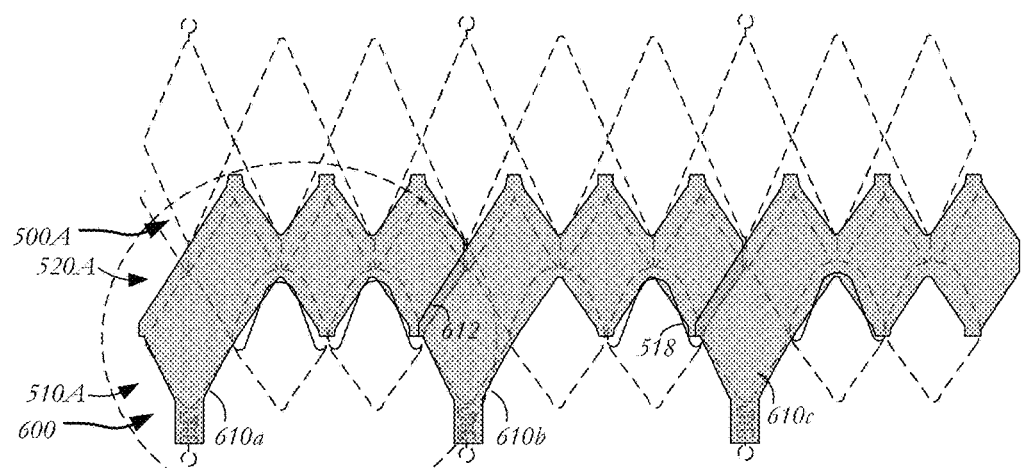
FIGS. 6A and 6B are highly schematic developed views of one example of a cuff configured for coupling to the stent of FIG. 5A.
Figure 6B:
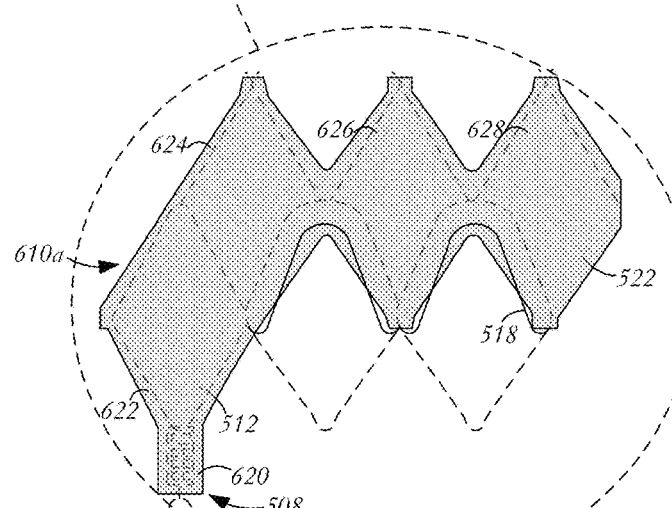

As shown in FIGS. 6A and 6B, a cuff 600 may be disposed over a portion of stent 500A. As illustrated, cuff 600 includes three separate segments 610a-c that are disposed over portions of the first and second rows of cells 510A, 520A and joined together at seams 612. By using a cuff formed of three segments, greater flexibility is provided for making finer adjustments to facilitate the assembly process. FIG. 6B illustrates cuff segment 610a in greater detail, cuff segments 610B and 610c being substantially the same. As shown, cuff segment 610a includes a first portion 620 sized to be disposed over commissure feature 508, a second portion 622 for covering symmetric cell 512 of first row 510A, and three substantially equal third portions 624,626,628 for covering three cells 522 of second row 520A. It will be understood that cuff 600 may be disposed on either the luminal or the abluminal surface of stent 500A and that the shape of the cuff may be modified as needed for a stent having a twelve-cell configuration. Additionally, a unitary cuff may be used instead of the three-segmented example shown. When disposed on the abluminal surface of stent 500A, cuff segment 610a may be configured to allow engaging arms 518 to extend therethrough to reach and couple to the native valve leaflets. Thus, engaging arms 518 are preferably unobstructed by cuff 600.

Figure 7A:
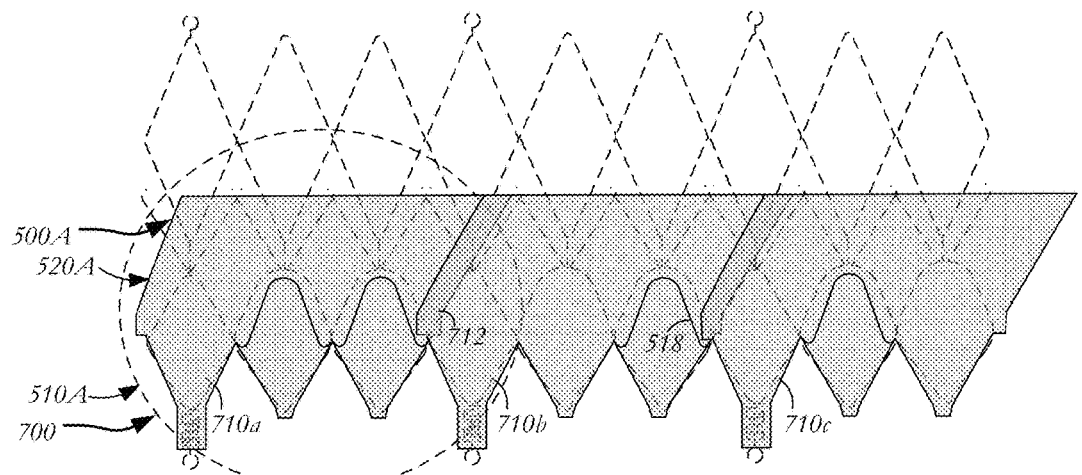
FIGS. 7A and 7B are highly schematic developed views of another example of a cuff configured for coupling to the stent of FIG. 5A.
Figure 7B:
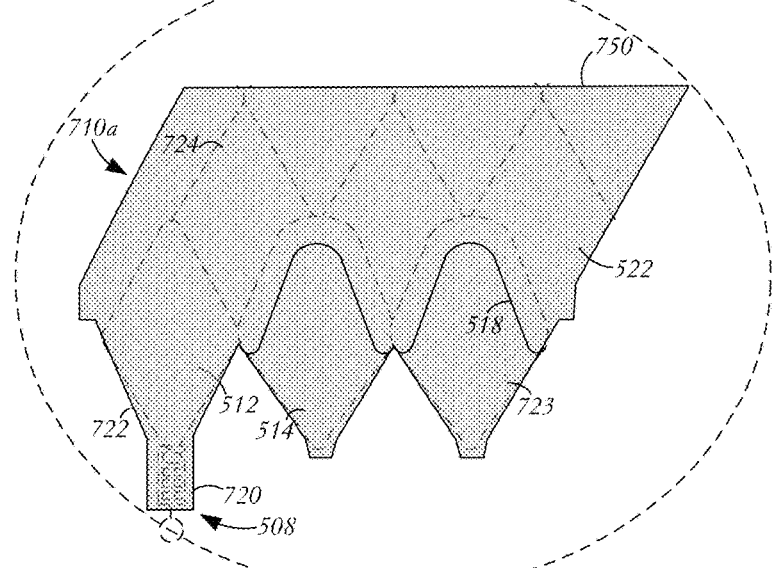

In another variation shown in FIGS. 7A and 7B, cuff 700 may be disposed over a portion of stent 500A. As illustrated, cuff 700 includes three separate segments 710a-c that are disposed over portions of the first and second rows 510A, 520A and joined together at seams 712. The differences between cuff 700 and cuff 600 described above are more readily identifiable by looking at the detailed view of FIG. 7B. As shown, cuff segment 710a includes a first portion 720 sized to be disposed over commissure feature 508. Second portion 722 covers symmetric cell 512 of first row 510A and includes two additional peaks 723 for covering asymmetric cells 514. A third portion 724 covers cells 522 of second row 520A and has a substantially straight edge 750 that runs horizontally across the lower corners of cells 522. Cuff 700 is shaped to allow engaging arms 518 to extend over the cuff and couple to the native valve leaflets. Cuff segments 710b and 710c may have the same configuration as cuff segment 710a.

Figure 8A:
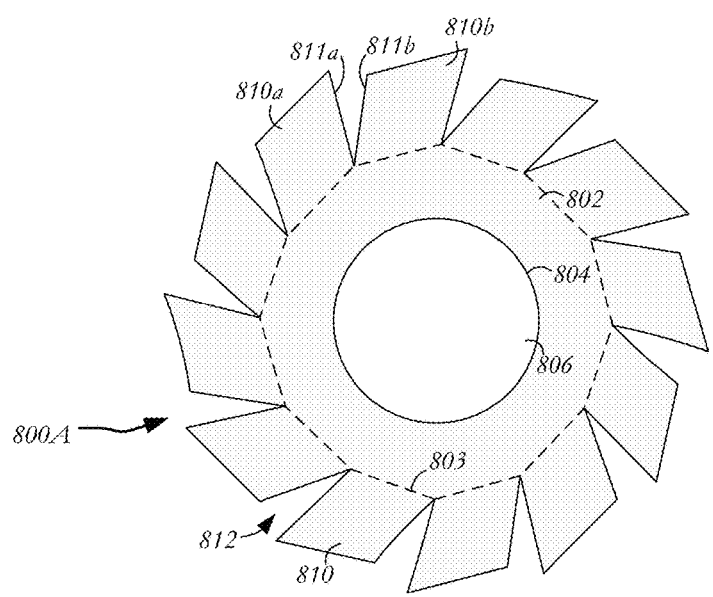
FIG. 8A is a highly schematic top view of a skirt for a prosthetic heart valve.

In addition to the cuff, a skirt may be disposed over the third row of cells 530A,530B to cover flared portion 450 of the stent. FIG. 8A illustrates one example of a skirt 800A configured to cover the third row of cells in a twelve-cell stent configuration (e.g., stent 500B of FIG. 5B). For the sake of clarity, skirt 800A will be described as having multiple portions or components. It will be understood, however, that the skirt may be formed of a single piece of tissue, fabric or polymeric material cut into a predetermined shape and that the portions or components described herein are only indicated for the sake of description and may not be readily discernible from the whole.

As shown, skirt 800A generally includes a hub 802 having a number of sides 803. Hub 802 is shown in the shape of a dodecagon in order to complement a twelve-celled stent. A circular cutout 804 is formed in the center of hub 802 to form void 806 for accepting a portion of the stent. In at least some examples, cutout 804 is formed having a circumference approximately equal to the circumference of a fully expanded stent at the second row of cells. A plurality of quadrilateral tabs 810 extend from the sides of hub 802. In the case of a dodecagon hub, twelve quadrilateral tabs 810 are formed around the perimeter of the hub, one extending from each side 803 of hub 802.

Figure 8B:
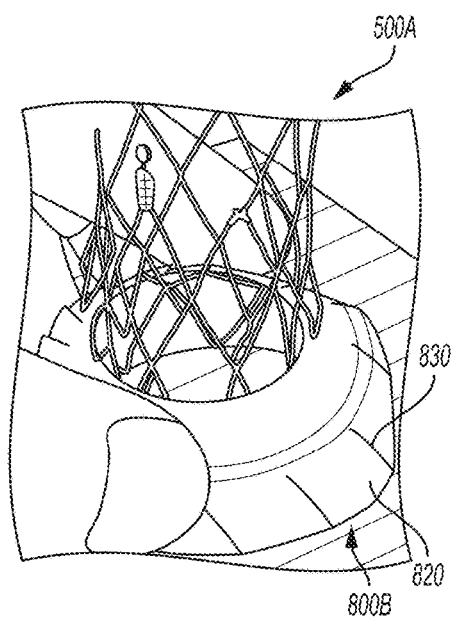
FIGS. 8B-C are a highly schematic top view of a skirt and photographs showing the assembly of a mock skirt onto a stent.
Figure 8C:
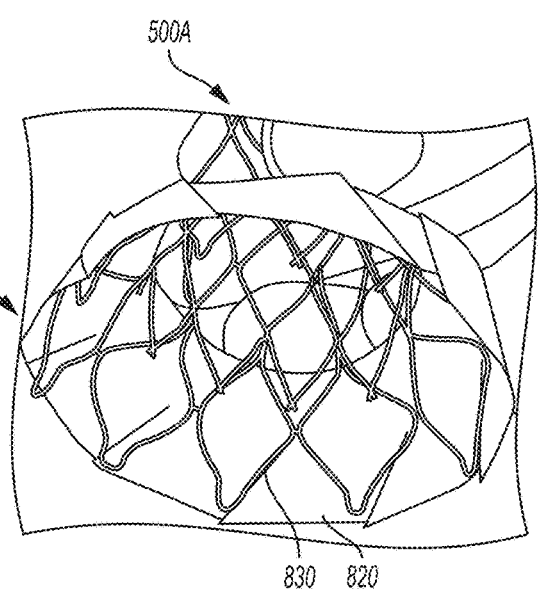

Due to the desired increasing diameter of flared portion 450 of the stent, triangular slits 812 are provided between quadrilateral tabs 810. However, when fully assembled to the stent, edges 811a,811b of adjacent quadrilateral tabs 810a, 810b will be sewn or otherwise coupled together to close slits 812. FIGS. 8B and 8C are photographs illustrating the assembly of a mock skirt 800B having nine quadrilateral tabs 820 to a stent having nine cells in each row. For the sake of clarity, the valve assembly including the cuff and the leaflets is not shown. Quadrilateral tabs 820 are coupled to one another at seams 830 to form a continuous surface. It will be understood that quadrilateral tabs 820 may be formed such that seams 830 align with struts of stent 500A as shown.

Figure 9A:
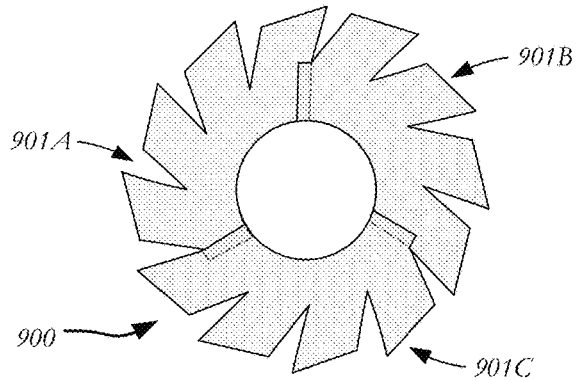
FIGS. 9A-C are a highly schematic top views of several variants of a skirt and the portions used to form same.
Figure 9B:
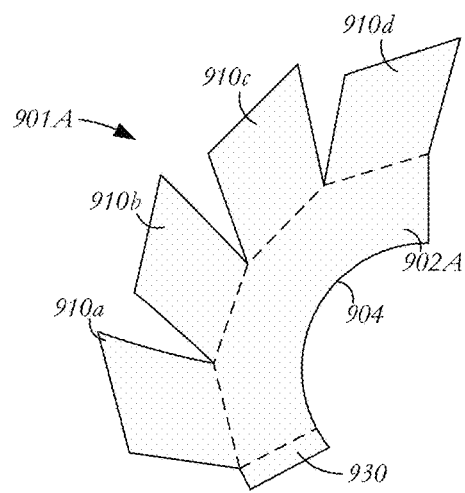
Figure 9C:
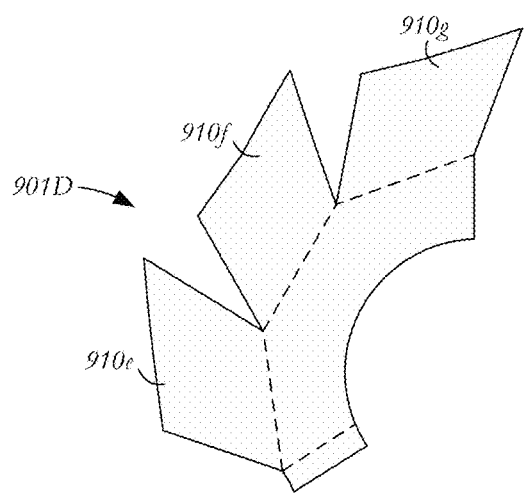

Instead of being formed as a single piece of material, a skirt may be formed in multiple segments. As seen in FIG. 9A, skirt 900 is formed of three equal segments 901A-C. As shown in FIG. 9B, each segment 901A-C may include a fraction of a hub, such as portion 902A defining an arc 904. Each portion 901A-C may also include a number of quadrilateral tabs 910a-d extending from portion 902A. It will be understood that each of segments 901A-C may be formed to be substantially the same size and may include the same number of quadrilateral tabs. An optional coupling 930 may be added to each of segments 910A-C and configured to overlap with an adjacent segment to add integrity to the assembly. It will be understood that variations are possible by changing the size and/or shape of the segments. For example, segments 901D, one of which is shown in FIG. 9C, may be formed to complement a stent of nine cells per row by having only three quadrilateral tabs 910e-g each.

Figure 10:
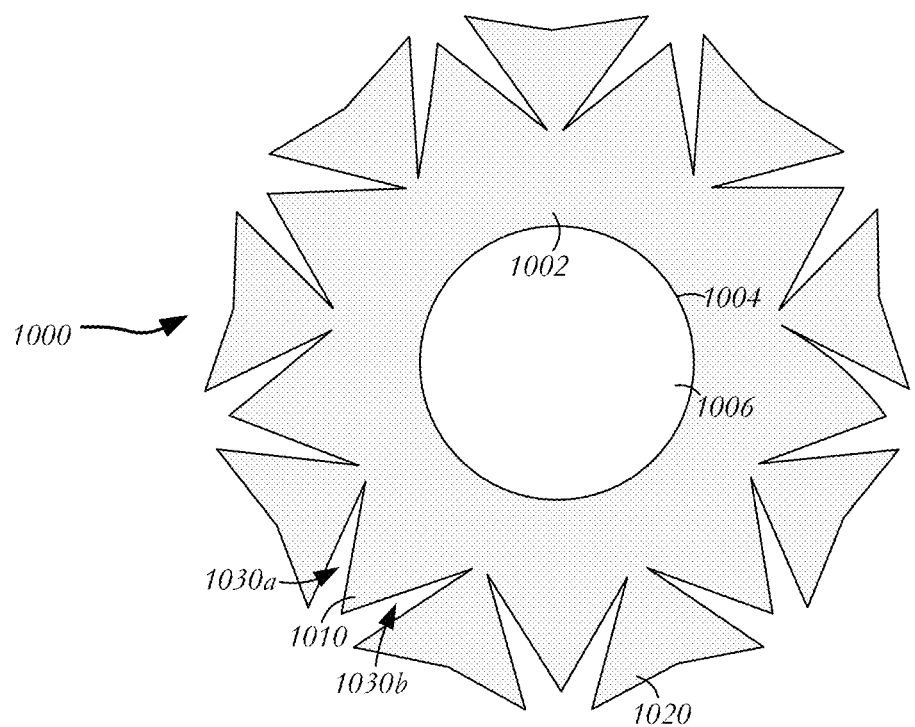
FIG. 10 is a highly schematic top view of another example of a skirt having multiple slits for reduced puckering at the seams.

In another variation, shown in FIG. 10, skirt 1000 includes more slits to reduce puckering at the seams. Similar to skirt 800A, skirt 1000 includes a hub 1002 having circular cutout 1004 at its center to form void 1006 for accepting a portion of the stent. Extending from hub 1002 and disposed on its perimeter are a series of alternating wedges including first wedges 1010 and second wedges 1020. In the examples shown, first wedges 1010 are substantially triangular and are attached at an edge of the triangle to hub 1002, and second wedges 1020 are substantially triangular and are attached to hub 1002 at a point of the triangle. Collectively, wedges 1010 and 1020 define a series of triangles that alternate in their connection to hub 1002. Each first wedge 1010 is disposed between adjacent second wedges 1020 and spaced from the second wedges by slits 1030a, 1030b. When fully assembled, edges of first and second wedges 1010, 1020 adjoin to one another to provide a continuous layer over a row of cells forming a flared portion 450. It will be understood, however, that the shapes of first and second wedges 1010, 1020 may be varied from the shapes shown and described herein and that skirt 1000 may, for example, include a series of wedges in the shape of triangles instead of concave quadrilaterals that are arranged so that each triangle is inverted with respect to an adjacent triangle.

Figure 11:
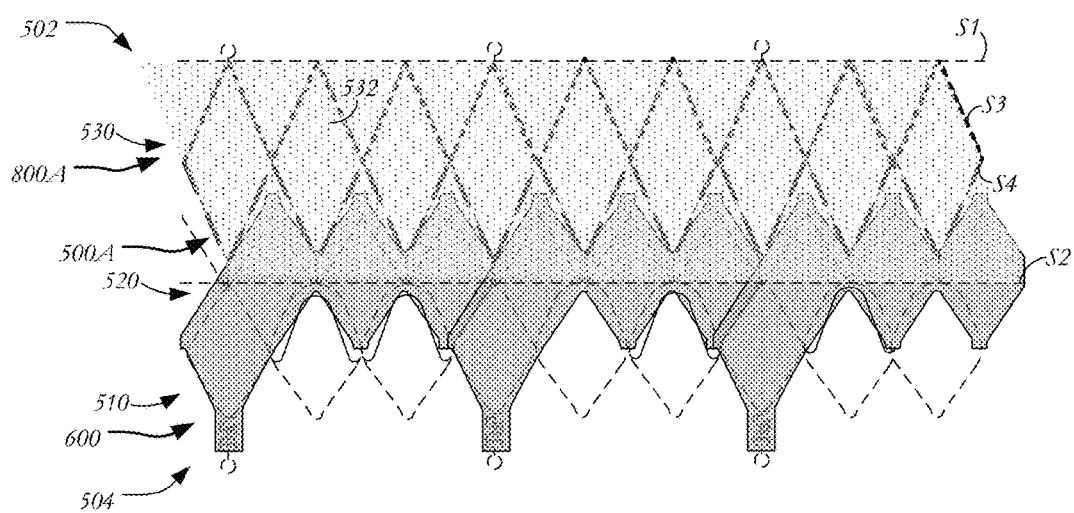
FIG. 11 is a highly schematic developed view of one example of a stent having a flared portion and a plurality of engaging arms with a skirt and a cuff coupled to the stent.

FIG. 11 illustrates one possible suture pattern for attaching a skirt, such as skirt 800A, to stent 500A having cuff 600. A first suture pattern S1 may be formed across the tops of cells 532 in third row of cells 530A at inflow end 502 of stent 500A, and around the circumference of the stent to attach skirt 800A to the stent. A second suture pattern S2 may be formed parallel to the first suture pattern S1 and across the ends of cells 512, 514 in first row of cells 510A and approximately halfway through cells 522 in second row of cells 520A. A third suture pattern S3 may consist of a zigzag pattern along the upper half of enlarged cells 532 of third row of cells 530A, and a fourth suture pattern S4 may form a second zigzag pattern along the lower half of enlarged cells 532, the fourth suture pattern S4 being a mirror image of the third suture pattern S3.

A fully assembled prosthetic heart valve 1200 is shown in FIG. 12A and includes stent 500A having inflow end 502 and outflow end 504. Inflow and outflow end views of prosthetic heart valve 1200 are shown in FIGS. 12B and 12C, respectively. Cuff 600 is disposed on a portion of stent 500A adjacent outflow end 504 and skirt 800A is disposed on the flared portion 450 of stent 500A adjacent inflow end 502, as described above with reference to FIG. 11. Additionally, three leaflets 1202 have been added to the interior of stent 500A and attached to commissure features 506 and to selected struts of stent 500A and/or cuff 600 to form a valve assembly as known in the art. Engaging arms 518 may also extend toward inflow end 502 and clip onto, or otherwise couple to, native valve leaflets to aid in anchoring stent 500A to the surrounding tissue. Though cuff 600 covers many cells of stent 500A, engaging arms 518 remain unobstructed to adequately perform their function. When deployed at the mitral valve position, prosthetic heart valve 1200 allows flow of blood from atrium 122 to left ventricle 124 and impedes blood backflow from left ventricle 124 to left atrium 122. Flared portion 450 may be disposed at least partially within the native valve annulus and/or left atrium 122 to anchor prosthetic heart valve 1200 (e.g., reduce the possibility of prosthetic heart valve 1200 migrating into left ventricle 124) and/or seal regions around prosthetic heart valve 1200 to reduce paravalvular leakage.

Figure 13:
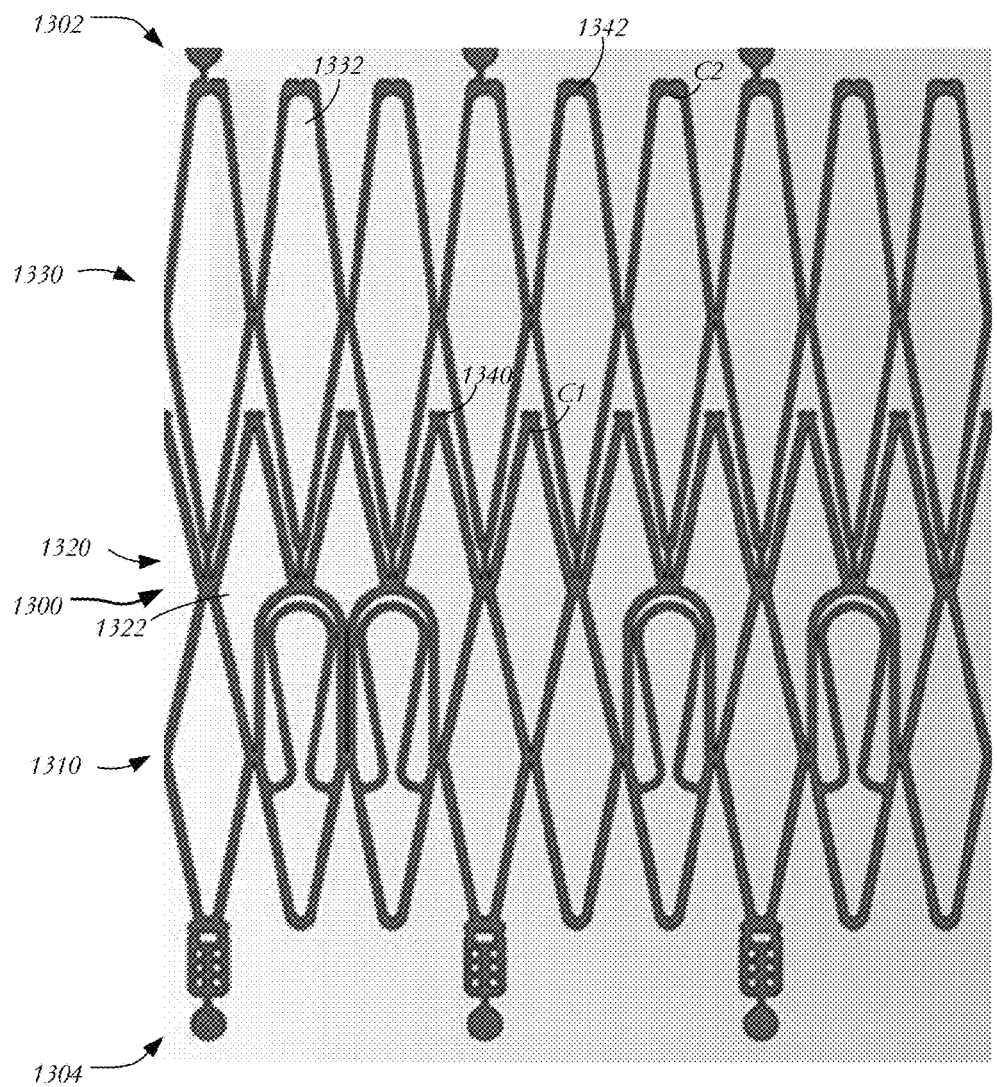
FIG. 13 is a developed view of one example of a stent having multiple horseshoes to aid in suturing.

Several variations of the stent for a prosthetic heart valve are possible. For example, FIG. 13 illustrates stent 1300 extending generally between inflow end 1302 and outflow end 1304 and having three rows of cells 1310,1320,1330, similar to the cells of stent 500A described above with reference to FIG. 5A. As shown, each row includes nine cells. The main difference between stent 500A and stent 1300 is the inclusion of horseshoes 1340,1342 to aid in suturing stent 1300 to a cuff and a skirt. Specifically, corners C1 of cells 1322 closest to inflow end 1302 include first horseshoes 1340 to prevent slippage of sutures when coupling stent 1300 to a cuff, and corners C2 of enlarged cells 1332 closest to inflow end 1320 include second horseshoes 1342 to prevent slippage of sutures when coupling stent 1300 to a skirt.

Figure 14A:
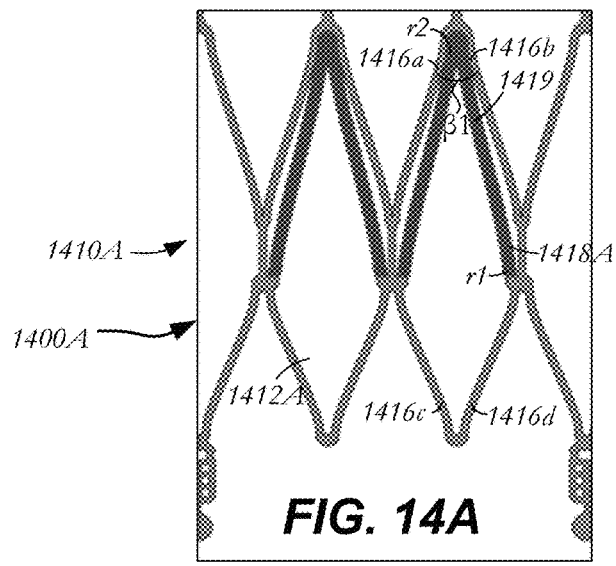
FIGS. 14A and 14B are developed views showing portions of a stent having engaging arms of different shapes.

The shape of the engaging arms may also be modified in several ways. In the simplest configuration, shown in FIG. 14A, stent 1400A includes a first row 1410A of cells 1412A. Each substantially diamond-shaped cell 1412A is composed of four struts 1416a-d joined to one another as shown, struts 1416a and 1416b forming an angle β1 therebetween. Nested engaging arms 1418A are formed of two substantially straight struts 1419 that are coupled to struts 1416c and 1416d at first ends r1 and to each other at second ends r2. Because of the shape of cells 1412A there is little room to form engaging arms 1418A resulting in a sharp tip at second ends r2 and a tight angle at first ends r1.

Figure 14B:
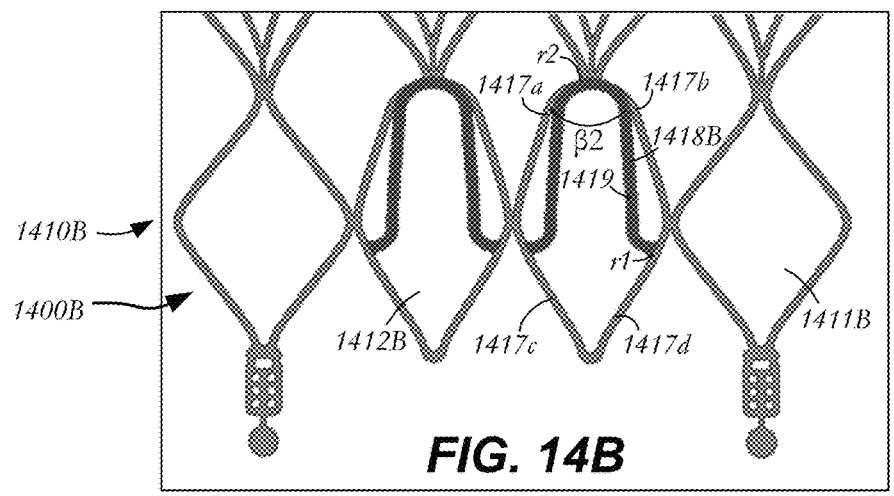

Instead of laser cutting a tube to create a stent in a collapsed state, the tube may be laser cut to create a stent in a partially expanded state. Cutting a stent from a larger diameter tube provides a larger area inside the cells of the stent to form engaging arms. Stent 1400B of FIG. 14B has been formed using this method and generally includes first row of cells 1410B having first cells 1411B and second cells 1412B, second cells 1412B being formed of struts 1417a-d. First cells 1411B that will not receive engaging arms may be substantially diamond-shaped, while second cells 1412B that receive engaging arms have a second shape that does not form a diamond. Specifically, struts 1417a and 1417b of cell 1412B may form a slight curvature such that the upper portion of cell 1412B is rounded and forms an angle β2, larger than angle β1, for receiving engaging arms. With the larger angle β2, an engaging arm may be formed with a curved loop 1419 having a smooth surface at position r2 that would be less traumatic if brought in contact with body tissue. Additionally, curved loop 1419 includes a wider takeoff at position r1 to reduce or eliminate a pinch point, resulting in less of a stress concentration on the anatomy that is contacted and easier loading within a delivery device.

As described in the previous examples, engaging arms are not disposed within each cell of first row 1410B. Thus, in forming a stent having engaging arms, the various features of stent 1400B may be cut from a metal tube under different conditions. For example, cells 1411B that do not have engaging arms 1418B may be cut when the tube is in a radially collapsed condition, and cells that include engaging arms 1418B may be cut when the tube is in a partially expanded condition. This approach avoids the need for cutting stent 1400B out of a large tube as the large tube can be expensive and more difficult to manufacture. Selectively cutting portions in the collapsed and partially expanded conditions allows for manufacturing the configurations as shown out of a relatively small diameter of tubing.

Figure 15:
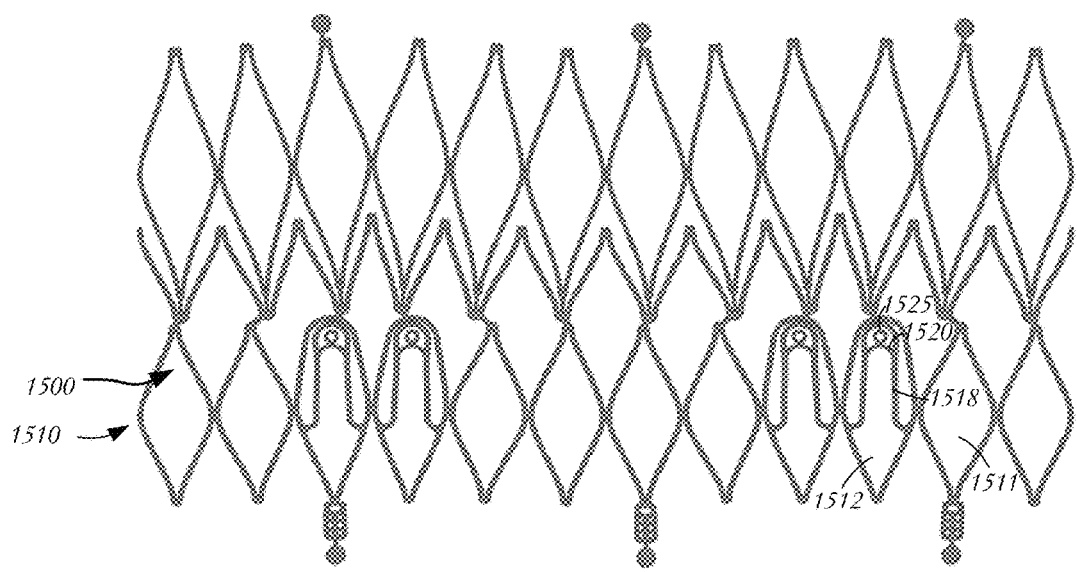
FIG. 15 is a developed view of one example of a stent having circular supports for accepting radiopaque markers.

In another variation shown in FIG. 15, stent 1500 may include features to aid in visualization during deployment. Stent 1500 may be substantially similar to stent 500A described above, and may include a first row 1510 of cells having first cells 1511 and second cells 1512, second cells 1512 including engaging arms 1518 therein. The main difference between stent 1500 and stent 500A is the presence of a bridging strut 1520 extending between the struts forming each engaging arm 1518 as shown. Bridging struts 1520 include a circular support 1525 for accepting a radiopaque marker (e.g., tantalum markers) to help make engaging arms 1518 more visible under fluoroscopy and/or echocardiography. Thus, the orientation of stent 1500 with respect to the native valve annulus may be more accurately detected so that engaging arms 1518 may be aligned with the native valve leaflets.

In some embodiments, a prosthetic heart valve having an inflow end and an outflow end includes a collapsible and expandable stent including a plurality of cells arranged in rows, each of the rows extending around a circumference of the stent, at least one of the rows forming a flared portion having a diameter that is larger than diameters of others of the rows, the stent further including engaging arms disposed adjacent the outflow end and extending toward the inflow end, the engaging arms being configured to couple to heart tissue to anchor the stent. A collapsible and expandable valve assembly is disposed within the stent and having a plurality of leaflets.

In some examples, at least one of the rows includes symmetric cells and asymmetric cells; and/or at least one of the rows includes enlarged cells for forming the flared portion; and/or each of the rows includes nine cells; and/or each of the rows includes twelve cells; and/or each of the engaging arms is nested within an asymmetric cell; and/or the engaging arms include two engaging arms for coupling to each native valve leaflet at a site of implantation; and/or the flared portion forms an angle of between about 120 degrees and about 180 degrees with respect to a longitudinal axis of the stent; and/or the valve further includes a cuff disposed over at least two rows of the stent and a skirt disposed over at least one row of the stent; and/or the cuff is divided into three segments that are joined together at seams; and/or the cuff is integrally formed from a single piece of material; and/or the valve further includes a radiopaque marker connected to at least one of the engaging arms; and/or the stent further includes a plurality of horseshoes formed on one end of selected cells in at least two of the rows.

In some embodiments a prosthetic heart valve having an inflow end and an outflow end, includes a collapsible and expandable stent including a plurality of cells arranged in rows, each of the rows extending around a circumference of the stent, the rows including a first row of having a first diameter and a second row of cells having a second diameter, the second diameter being larger than the first diameter, a collapsible and expandable valve assembly disposed within the stent and having a plurality of leaflets, an annular cuff disposed over cells of the first row of cells, and an annular skirt disposed over cells of the second row of cells.

In some examples, the skirt includes a plurality of quadrilateral tabs with a triangular slit between each adjacent pair of tabs; and/or the plurality of quadrilateral tabs includes nine tabs; and/or the plurality of quadrilateral tabs includes a quadrilateral tab corresponding to each cell in the second row of cells; and/or the skirt includes three segments that are sewn together; and/or the skirt includes first wedges, second wedges, and a plurality of slits defined between the first and second wedges; and/or Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve having an inflow end and an outflow end, comprising:
   a collapsible and expandable stent including a plurality of cells arranged in rows, each of the rows extending around a circumference of the stent, at least one of the rows forming a flared portion having a diameter that is larger than diameters of others of the rows, at least one of the rows including a plurality of cells having a first shape and a plurality of cells having a second shape different than the first shape, the stent further including engaging arms disposed adjacent the outflow end and extending toward the inflow end, the engaging arms being configured to couple to heart tissue to anchor the stent; and
   a collapsible and expandable valve assembly disposed within the stent and having a plurality of leaflets.

2. The prosthetic heart valve of claim 1, wherein at least one of the rows includes symmetric cells and asymmetric cells.

3. The prosthetic heart valve of claim 2, wherein the symmetric cells are substantially diamond shaped and the asymmetric cells comprise a curved portion.

4. The prosthetic heart valve of claim 1, wherein at least one row forming the flared portion includes cells having a dimension along the circumference of the stent that is larger than a dimension along the circumference of the stent of cells of other rows.

5. The prosthetic heart valve of claim 1, wherein each of the rows includes nine cells.

6. The prosthetic heart valve of claim 1, wherein each of the rows includes twelve cells.

7. The prosthetic heart valve of claim 1, wherein each of the engaging arms is nested within a respective one of the cells having the second shape.

8. The prosthetic heart valve of claim 1, wherein the engaging arms are positioned on the stent so that, in use, two engaging arms are arranged to couple to each native valve leaflet at a site of implantation.

9. The prosthetic heart valve of claim 1, wherein the flared portion forms an angle of between about 120 degrees and about 180 degrees with respect to a longitudinal axis of the stent.

10. The prosthetic heart valve of claim 1, further comprising a cuff disposed over at least two rows of the stent and a skirt disposed over at least one row of the stent.

11. The prosthetic heart valve of claim 10, wherein the cuff comprises three segments that are joined together at seams.

12. The prosthetic heart valve of claim 10, wherein the cuff is integrally formed from a single piece of material.

13. The prosthetic heart valve of claim 1, further comprising a radiopaque marker connected to at least one of the engaging arms.

14. The prosthetic heart valve of claim 1, wherein the stent further includes a plurality of horseshoes formed on one end of selected cells in at least two of the rows.

15. A prosthetic heart valve having an inflow end and an outflow end, comprising:
   a collapsible and expandable stent including a plurality of cells arranged in rows, each of the rows extending around a circumference of the stent, the rows including a first row of cells having a first diameter and a second row of cells having a second diameter, the second diameter being larger than the first diameter, the first row including a plurality of cells having a first shape and a plurality of cells having a second shape different than the first shape the stent further including engaging arms nested within at least one of the plurality of cells having the second shape;
   a collapsible and expandable valve assembly disposed within the stent and having a plurality of leaflets;
   an annular cuff disposed over cells of the first row of cells; and
   an annular skirt disposed over cells of the second row of cells.

16. The prosthetic heart valve of claim 15, wherein the skirt includes a plurality of quadrilateral tabs with a triangular slit between each adjacent pair of tabs.

17. The prosthetic heart valve of claim 16, wherein the plurality of quadrilateral tabs includes nine tabs.

18. The prosthetic heart valve of claim 16, wherein the plurality of quadrilateral tabs includes a quadrilateral tab corresponding to each cell in the second row of cells.

19. The prosthetic heart valve of claim 15, wherein the skirt includes three segments that are sewn together.

20. The prosthetic heart valve of claim 15, wherein the skirt includes first wedges, second wedges, and a plurality of slits defined between the first wedges and the second wedges.

* * * * *